(12) United States Patent
Madden et al.

(10) Patent No.: US 7,391,333 B2
(45) Date of Patent: Jun. 24, 2008

(54) SYSTEM FOR MONITORING QUALITY OF WATER SYSTEM

(75) Inventors: Terrance P. Madden, Syracuse, NY (US); Christopher Campbell, Rome, NY (US); Cornelius Murphy, Syracuse, NY (US); Michael R. Brower, Syracuse, NY (US)

(73) Assignee: Source Sentinel, LLC, Syracuse, NY (US)

( * ) Notice: Subject to any disclaimer, the term of this patent is extended or adjusted under 35 U.S.C. 154(b) by 192 days.

(21) Appl. No.: 11/236,088

(22) Filed: Sep. 27, 2005

(65) Prior Publication Data

US 2007/0257806 A1 Nov. 8, 2007

Related U.S. Application Data

(60) Provisional application No. 60/613,619, filed on Sep. 27, 2004.

(51) Int. Cl.
*G01N 33/00* (2006.01)
*G08B 21/00* (2006.01)

(52) U.S. Cl. ............... 340/603; 210/739; 73/61.41
(58) Field of Classification Search ................ 210/615, 210/743, 739; 340/603; 73/61.41
See application file for complete search history.

(56) References Cited

U.S. PATENT DOCUMENTS 4,246,101 A * 1/1981 Selby, III ............... 210/615

| | | | | |
|---|---|---|---|---|
| 4,323,992 A * | 4/1982 | Tobin, Jr. | ............... | 367/108 |
| 6,560,543 B2 * | 5/2003 | Wolfe et al. | ............... | 702/22 |
| 6,591,166 B1 | 7/2003 | Millett | | |
| 6,954,701 B2 * | 10/2005 | Wolfe | ............... | 702/22 |
| 2003/0236649 A1 | 12/2003 | Kodukula | | |
| 2005/0043059 A1 * | 2/2005 | Petite et al. | ............... | 455/557 |

FOREIGN PATENT DOCUMENTS

| | | |
|---|---|---|
| DE | 299 12 126 U1 | 10/1999 |
| EP | 0 334 113 A | 9/1989 |
| EP | 0 707 247 A | 4/1996 |
| JP | 01 315393 A | 12/1989 |
| WO | WO 95/26008 A | 9/1995 |
| WO | WO 97/26606 A | 7/1997 |

* cited by examiner

*Primary Examiner*—Walter D. Griffin
*Assistant Examiner*—Cameron J Allen
(74) *Attorney, Agent, or Firm*—George R. McGuire; Bond Schoeneck & King, PLLC

(57) ABSTRACT

A monitoring, detection and alarm for water systems includes a plurality of sensing components for detecting the presence of target contaminants in water and for measuring the overall quality of the water. The apparatus contains water sensing components, a database for storing sensor data and processors for data analysis using artificial intelligence. The apparatus provides control logic to take responsive action based on the results of the detection of the target contaminants. Responsive action includes, but is not limited to, generation of reports and alarm signals that are delivered in near real-time to users of the system.

27 Claims, 2 Drawing Sheets

SYSTEM FOR MONITORING QUALITY OF WATER SYSTEM

CROSS-REFERENCE TO RELATED APPLICATION

The present application claims priority to U.S. Provisional Application Ser. No. 60/613,619, filed Sep. 27, 2004, the entirety of which is hereby incorporated by reference.

FIELD OF THE INVENTION

This invention relates to an apparatus and method for monitoring the presence or absence of harmful biological, radiological, and/or chemical toxins and other compounds in water, and more particularly to an apparatus and method of monitoring the overall quality of water being used by many entities. These entities include, but are not limited to, military installations and their support structures, recreational entities (e.g., water parks, beaches, rivers), institutions (e.g., hospitals, schools, colleges, universities, federal and state buildings) and municipalities.

BACKGROUND OF THE INVENTION

The monitoring and detection of contaminants and other abnormal conditions in water systems is now a necessity in the United States and around the world. Ensuring a water system to be clean and safe has become a more visible public issue since the terrorist attacks of Sep. 11, 2001. Concern that water safety may be affected by potential terrorist activities has increased the awareness and emphasis on developing and deploying new sensing, analytical and decision making technologies, and in particular, ones that make possible near-real time (NRT) monitoring and management of water quality.

Traditionally, water has been tested for presence of contaminants by taking a sample, such as filling a container with the water to be tested, and then transporting that sample to a remote laboratory for analysis. The results are then reported back to the operating entity. By the time results are available, the actions available to the agency responsible operating the water system will likely be limited to remedial actions, including costly measures to clean up the affected water system. If the contaminant is toxic, the lag time in response could contribute to catastrophic health results.

It is therefore essential to quickly and accurately detect and identify in near real-time a wide range of contaminants, including chemicals and radiological and infectious biological agents. Such a system must detect contaminants at very low concentration levels in water. The increased complexity of the sensor arrays necessary for near real time detection at low concentrations raises a new issue: the need to integrate and interpret multiple data sources rapidly and determine the correct response for the affected water system. The total amount of information available from multiple sensor arrays may be too complex for the end user to interpret in the time allowed. This generally causes the water system operator to ignore some information to focus on data that is most familiar, and may lead to erroneous interpretations of the available data.

There are some examples in the prior art of water quality fluorometer sensors. The method described in U.S. Pat. No. 6,064,480 entitled, "Method Of Optical Particle Counting For Water Mixed Lubricant," issued on May 16, 2000 to Mountain et al., is confined to monitoring solid particles greater than about 5 microns in size. A light detector generates an electrical signal responsive to the passage of a light obstructing particle between the light detector and a light emitter. The apparatus described in U.S. Pat. No. 6,141,097 entitled, "Optical Measurement Of Marine Conditions," issued on Oct. 31, 2000 to Herman, is confined to detecting organisms or particle sizes above about 2.5 µm. The apparatus uses an optical system in which the receiver comprises an array of photo-sensor elements wherein the size of the photo-sensor elements is selected to be greater than the smallest organism and smaller than the largest organism to be measured. This apparatus generates an output signal providing an average level representative of turbidity in the water and a changing attenuated level caused by the passage of an organism.

The method described in U.S. Pat. No. 6,255,118 B1 entitled, "Method For Using An All Solid-State Fluorometer In Industrial Water System Applications," issued on Jul. 3, 2001 to Fehr et al., is confined to the monitoring of fluorescent tracers that are particularly suitable for industrial water sample stream applications. A solid-state diode laser is used to excite the fluorescent tracers and a photodiode detects the scattered light. The output from the photodiode is amplified to produce an output voltage proportional to the quantity of fluorescence striking the photodiode detector.

Notwithstanding the usefulness of the prior art, what is needed is a system that analyzes a plurality of various sensor signals to detect in real-time or near real-time the presence of any of a number of organic and chemical compounds that pose a threat to water systems, the system having built-in redundancies and near real-time communication capabilities. What also is needed is a system that can integrate a large amount of analytical data provided by sensors, evaluate the data, predict water quality of a given water system, and provide an alert that is triggered in the event a hazardous condition is detected.

SUMMARY OF THE INVENTION

It is a principal object and advantage of the present invention to provide an apparatus to detect the presence of contaminants in a water system and provide a real time alert to water system operators.

It is another object and advantage of the present invention to predict the occurrence of abnormal conditions in a water system before a deviation in normal baseline parameters is detected and provide a prompt alarm of the impending occurrence so action can be taken to prevent the abnormal condition.

It is still another object and advantage of the present invention to provide an apparatus that will compute and analyze signals that are generated from numerous sensor arrays and provide real-time or near real-time notification to the appropriate users.

Yet another object and advantage of the present invention is to provide an apparatus that will automatically generate a recommended mitigation plan in response to the predicted occurrence of an abnormal condition or the detected presence of a contaminant.

Other objects and advantage of the present invention will in part be obvious, and in part appear hereinafter.

In accordance with the foregoing objects and advantages, the system according to the present invention provides a NRT system that integrates commercially-available sensors that monitor data related to specific water quality concerns. The present invention includes a flexible and adaptable sensor suite, seamless communication, and intelligent inference-driven decision making for fixed or mobile (e.g., floating) platforms. The result is a NRT system that provides scientifically valid data that can then be analyzed and used for decision making on vital water quality issues; the results of the analysis can then be rapidly communicated to the public or other interested parties to allow corrective actions to be taken, if necessary.

DETAILED DESCRIPTION OF THE INVENTION

Figure 1:
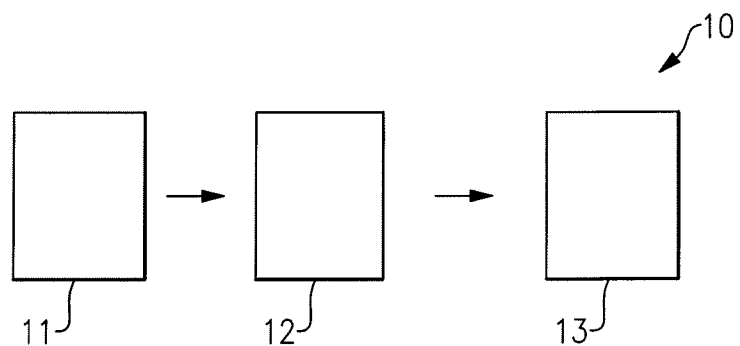
FIG. 1 is a high level schematic diagram of one aspect of the present invention.
Figure 2:
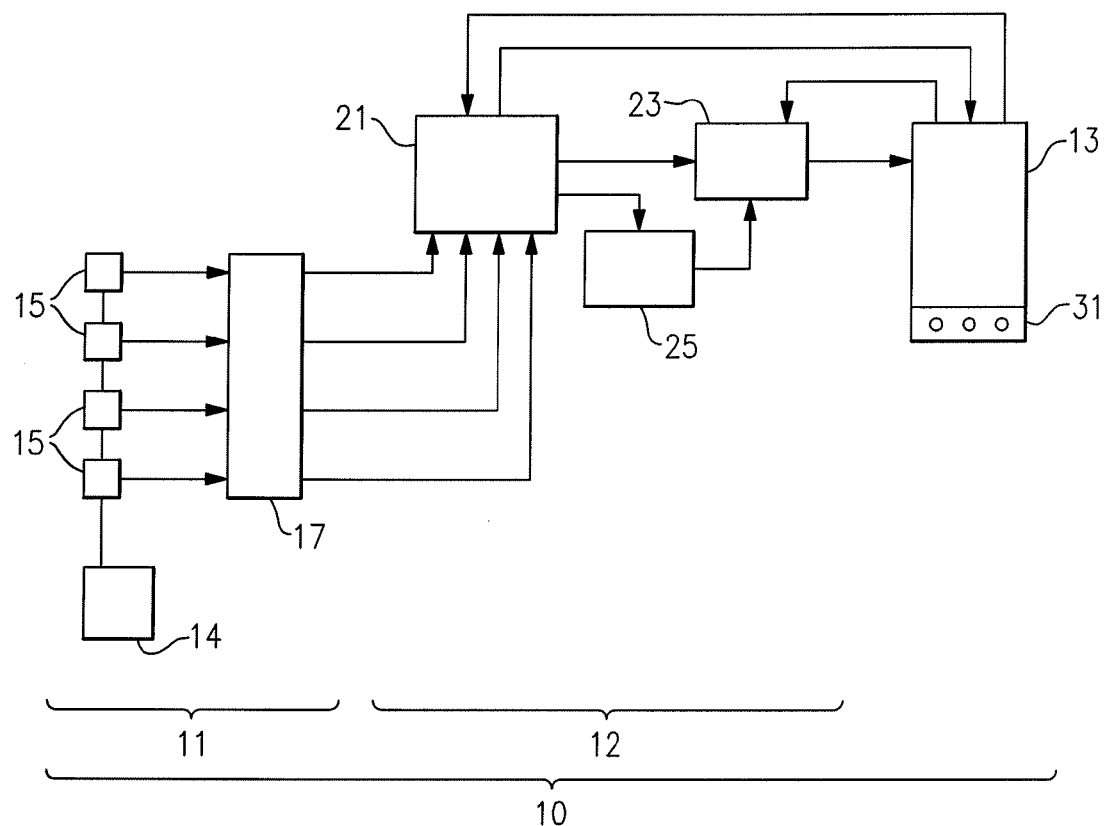
FIG. 2 is a schematic representational diagram of an embodiment of the present invention.
Figure 3:
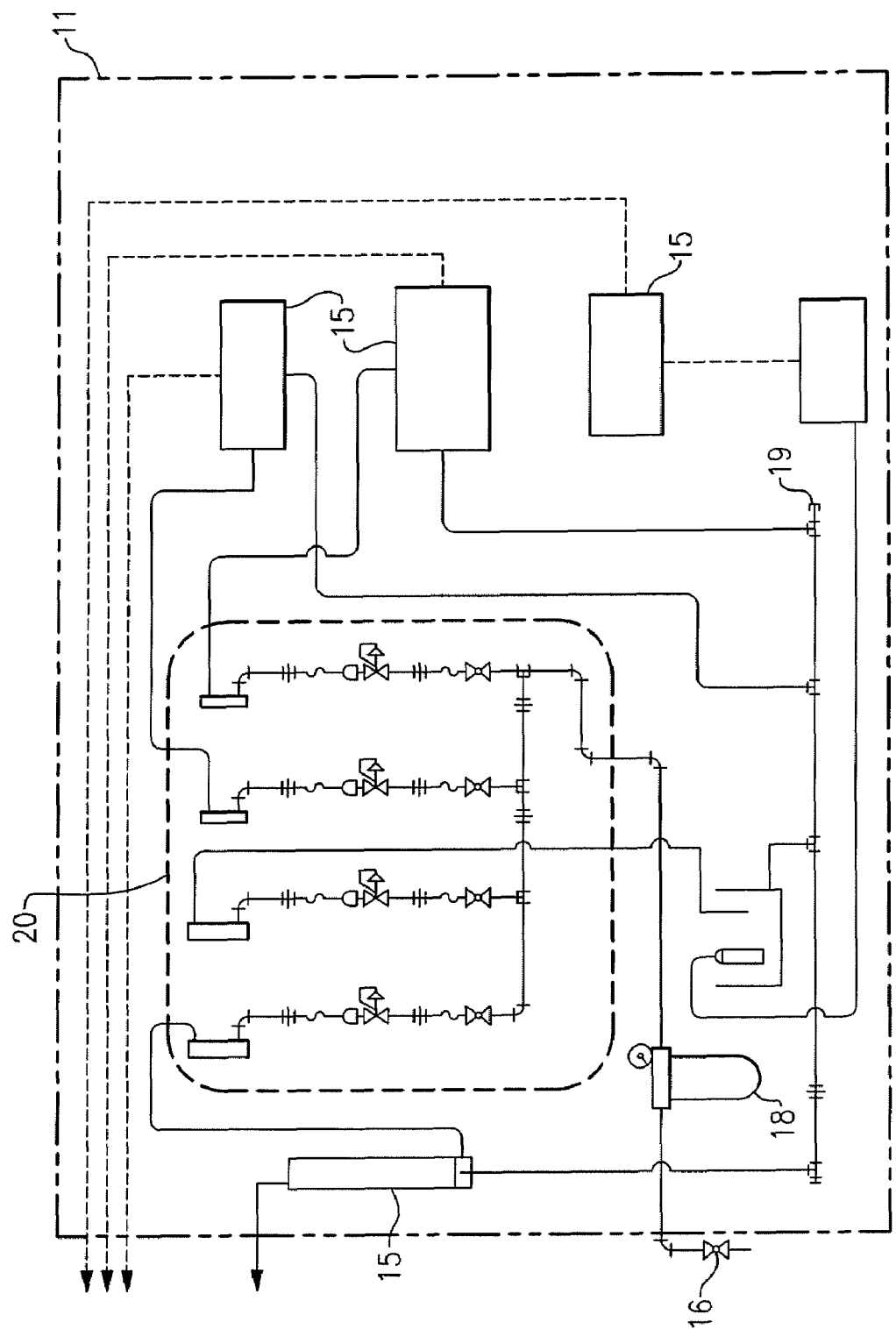
FIG. 3 is a schematic diagram of the monitoring module of the present invention.

Referring now to FIGS. 1 and 2, a water monitoring system 10 according to the present invention is schematically illustrated and generally comprises three modules, namely a monitoring module 11 that gathers water samples and performs tests on those samples to determine the presence or absence of a particular environmental parameter, a decision support module 12 for receiving data from monitoring module 11 that is representative of the presence or absence of the parameters being sensed and processing that data to determine a percent probability of a particular harmful condition being present in the water system being monitored based on the received and processed data, and a user interface module 13 that provides a visual and/or aural display indicative of the state of the water system being monitored, as will be described in greater detail hereinafter.

The monitoring module 11 comprises basic fluidics for handing flow control to the sensors 15. The fluidics include, for example, water intake 16, a filter 18 and a drain 19. The fluid handling is precisely calculated and controlled to determine the optimum detection limits and/or sensitivity of each integrated sensor instrumentation. Control of possible contaminant collection inside the hydraulic system is achieved by a distributing manifold 20. The monitoring module 11 preferably can expand to accommodate additional sensors 15 for detecting the presence or absence of additional contaminants and parameters.

Each sensor 15 is adapted for measuring and/or detecting a particular water system parameter, including the presence of selected chemicals, selected biological material and basic environmental parameters such as temperature, turbidity and pH (for purposes of this patent, any condition a sensor is adapted to detect will be generically referred to as an "environmental parameter"). Sensors such as the YSI 6600 series are acceptable, but others, including the Hydro Lab DS SX series, may also be substituted. The output from sensor 15 is either digital or analog, and if analog, must be processed through an analog-to-digital converter. Sensor 15 data is correlated with a clock 14 that is either internal to each sensor or external. Sensors 15 produce an output signal at a user selectable frequency, for example, once every second. The monitoring module 11 includes a sensor converter 17 to convert sensor 15 outputs into a form that can be stored and analyzed by the system 10. Sensor converter 17 is not necessary, however, provided that all of sensors 15 produce outputs in acceptable form in which case the data is transmitted directly from sensor 15 to decision support module 12 (for instance, sensor 15 may include data transmission means embedded therein).

Data output from the monitoring module 11 is provided on a predetermined periodic basis (e.g., once every minute, hour, day, etc.) via any well known data transport mediums, such as conventional copper telephone lines, co-axial cable lines, fiber, or wirelessly to the decision support module 12 for analysis. The decision support module 12 includes a relational database 21, artificial intelligence processor 25 and decision processor 23. Acceptable relational databases 21 include InTouch WonderWare or Intellution iHistorian. In the decision support module 12 data from the sensors 15 is provided to the relational database 21. The relational database 21 stores data from sensors 15, as well as historical information related to the specific water system where the system 10 is deployed. The artificial intelligence processor 25 analyzes the data stored in the relational database 21 by applying user-provided algorithms and domain knowledge to identify data trends, historical comparisons and deviations from baseline patterns. The sensors' 15 output is collected and analyzed in total, as illustrated in the examples to follow, thus allowing the system to determine a more accurate and appropriate response than would be achieved using a single sensor 15 or a simple threshold approach. The output of the artificial intelligence processor 25 is provided to the decision processor 23, which applies rules that are stored in the relational database 21 to determine if a contaminant or condition is present, in which case it generates an alarm that is communicated to the user interface module 13.

The artificial intelligence processor 25 performs redundancy verification and uses a combination of learning algorithms, intelligent agents and network structures, such as a Bayesian network structure and/or a neural network structure, to assess the inputs from the different sensors 15. The artificial intelligence processor 25 assigns weights to the inputs from the different sensors 15, analyzes the sensor data and applies actual sensor data to "learn" trends and anomalies related to the water system. Acceptable artificial intelligence processors 25 include the inference engines disclosed in U.S. Patent Application Ser. Nos. 60/663,950 and 60/663,793, both of which are hereby incorporated by reference. Redundancy verification ensures security and dramatically reduces false positive indications. The analysis is based upon data taken from multiple sensors 15 and is able to detect abnormalities in the water quality, determine the possible sources of the abnormalities, indicate the severity of the abnormalities, generate alarms and possible system control responses. Accuracy of the analysis is a result of evaluating a plurality of data inputs to identify threats and reduce false positives.

The artificial intelligence processor 25 uses inputs from sensors 15, historical information related to a specific water system, specialized algorithms, and domain knowledge of the environment being monitored to predict (within a specified mathematical confidence range) the chemical and/or biological threat to a water system. The artificial intelligence processor 25 learns from past events to predict impeding threats, preferably before the threat fully develops. The artificial intelligence processor 25 receives data from the sensors 15 and compares it to model patterns stored in the relational database 21.

One acceptable type of artificial intelligence processor 25, a Bayesian network, can analyze the model patterns based on comparisons to a general knowledge database that is built from existing information regarding water quality characteristics and the set of rules that water quality is patterned after. The incoming model patterns are compared to the existing general knowledge database for the specific rule set and the network recognizes particular patterns and then calculates the probability of potential problems. The software then evaluates using one type of probability matrix analysis and, dependent upon the results, generates reports and/or generates alarms to the appropriate authorities.

Some conditions in a water system may produce sensor data that so clearly requires an alarm that it is not necessary to analyze the data. For this reason, data from the sensors 15 is also provided directly to the decision processor 23 without analysis by the artificial intelligence processor 25. The decision processor 23 analyzes the received signals from each of the sensors 15 and applies rules to this data to determine if an alarm is necessary.

Detection, identification, and response to contaminants, such as algae, for example, *E. coli*, and microcystin are significantly enhanced by the use of the artificial intelligence processor 25. The artificial intelligence processor 25 assesses the inputs from several sensors 15. It then provides a probabilistic indication of the presence of a certain contaminant and an optimized operational strategy. The "knowledge" used to construct the artificial intelligence processor 25 is based on expertise provided by experts in the field of water chemistry. The domain knowledge defines the conditional relationships between the outputs of the system's sensors 15 and the presence of given contaminants.

The third module in the system 10 is a user interface module 13 that is connected to decision support module 12 via conventional data transport means, such as copper cable, coaxial cable, fiber or wireless. The user interface module 13 displays alarm status, mitigation plan information and independent sensor data related to the condition of the water system, as requested by the operator. According to one embodiment, the user interface module 13 uses a worldwide computer network to communicate with the relational database 21 and decision processor 23 to generate a display or alarm that is accessible by authorized users at locations remote from the water system. User interface module 13 also provides a keyboard, mouse or other data input means to allow a user to store data in relational database 21 or provide additional (or modified) rules to be applied by decision processor 23. The user interface module 13 provides information about the overall condition of the water system and can also be used to obtain individual sensor data.

The mitigation plan generated by the decision processor 23 can also be signaled to the appropriate authorities when the need arises based on a water system problem and determine an operational strategy for handling the problem. The user interface module 13 can also be used to display water quality management information, and suggested operational plans in order to be proactive before a larger problem develops.

According to one embodiment, the user interface module 13 uses color-coded outputs 31 to signal the presence or absence of a particular contaminant or condition. The user interface module 13 allows users to query the relational database 21 for specific information, for example, pH readings at a specific sensor location. Preferably, a system 10 according to the present invention incorporates encryption and security measures that prevent unauthorized access to system warnings and data, but still allow authorized users to access the system remotely (e.g., to have an off-site supervisor review information generated by the system).

In addition to providing real-time analysis of the likelihood a particular contaminant is present, a system 10 according to the present invention is also capable providing predictive analysis to provide warning that a specific condition is likely to occur in the water system in the future. When used as a predictive tool, the system 10 uses sensors 15 to detect data about the presence of certain chemicals and/or organisms in the water and environmental conditions of the water, which data is stored in the relational database 21. The artificial intelligence processor 25 generates model patterns from the data, which are analyzed for example by a Bayesian network. The artificial intelligence processor 25 output is provided to the decision processor 23, which compares the sensor data to historic data stored in the relational database 21 to determine the likelihood that a specific condition will occur in the water system in the future. If the decision processor 23 determines that the specific condition is likely or imminent, it generates an alarm at the user interface module 13 to notify the appropriate officials to take preventive action.

The user interface module 13 preferably provides color coded outputs 31 that indicate the condition of water system parameters to the water system operators. For example, a green output indicates that a parameter is safe; red indicates that a hazardous condition exists; yellow indicates presence of a condition that is not immediately dangerous, but which should be monitored closely. In addition, user interface module 13 allows water system operators to query the sensor 15 data stored in the relational database 21 to obtain specific information about one or more water system parameters. For example, water system operators can query the user interface module to determine the current and baseline levels of a specific chemical.

The user interface 13 also provides water system operators with instructions for correcting or mitigating detected conditions. For example, if the system 10 alarms because a hazardous condition has been detected, the user interface module 13 not only presents the alarm, but also can provide the water system operator with instructions to either eliminate the hazardous condition or minimize the risk it poses to users of the water system.

As previously described, communication within and between components of the system 10, for example between monitoring module 11 and decision support module 12 can be a variety of communication means, including wire, fiber optic cable, radio signals or a global, local, or wide area computer network. Thus, according to the present invention, sensors 15 are located in the water system being monitored, but other components of the system such as the decision support module 12 or individual components of the decision support module 12 may be located remotely.

While the present invention is described with reference to detecting organic and chemical target compounds in water handled by public suppliers, a practitioner in the art will recognize the principles of the present invention are applicable elsewhere particularly in the water distribution chain.

Using the toxin Microcystin as an example, the following table shows examples of the response generated (Microcystin, Cyanobacteria, Other problem) on several cases received from various sensors 15 (Biosensor, Chlorophyll, Temperature, pH, Dissolved Oxygen, Turbidity):

| Biosensor | False | True | True | True | False | True | False | True - toxin is detected |
| | | | | | | | | F - toxin is not detected |
| Chlorophyll | High | High | High | High | High | Normal | Normal | High - greater than 70 µg/L |
| | | | | | | | | Normal - 0-70 µg/L |

-continued

| | | | | | | | | |
|---|---|---|---|---|---|---|---|---|
| Temperature | High | High | High | High | High | Normal | High | High - greater than 30 deg C. Normal - 0-30 deg C. |
| pH | Normal | Normal | High | High | High | Normal | High | High - greater than 8.5 units Normal - 7-8.5 units |
| Dissolved Oxygen | Normal | Normal | Normal | High | High | Normal | Normal | High - greater than 15 mg/L Normal - 0-15 mg/L |
| Turbidity | Normal | Normal | Normal | High | High | Normal | High | High - greater than 20 NTU Normal - 0-20 NTU |
| Cyanobacteria | 45.1% | 93.0% | 99.4% | 100% | 100% | 0% | 9.14% | Above 10% - alert |
| Microcystin | 2.03% | 88.2% | 93.9% | 94.4% | 4.48% | 6.17% | 0.43% | Above 2% - alert |
| Other problem | 31.3% | 21.4% | 22.7% | 22.9% | 68.9% | 1.49% | 6.55% | Above 50% - alert |

In the first case, the sensor 15 did not detect Microcystin, but detected a high level of chlorophyll level (greater than 70 µg/L), high temperature (greater than 30 deg C.), normal pH (within range 7-8.5 units), normal Dissolved Oxygen ("DO") (within range 0-15 mg/L), and normal turbidity (within range 0-20 NTU). In response to data received from the sensors 15 and analysis by the artificial intelligence processor 25, the decision processor 23 determines that the probability of Cyanobacteria in the water is 45%, the probability of Microcystin in the water is 2.03%, and the probability of another problem (for example water taste problem) is 31.3%.

In the second case, the sensor 15 detected Microcystin, a high level of chlorophyll, high temperature, normal pH, normal DO, and normal turbidity. In response to data received from the sensors 15 and analysis by the artificial intelligence processor 25, the decision processor 23 determines that the probability of Cyanobacteria in the water is 93.0%, the probability of Microcystin in the water is 88.2%, and the probability of other problem (for example water taste problem) is 21.4%.

In the third case, the sensor 15 detected Microcystin, a high level of chlorophyll, high temperature, high pH, normal DO, and normal turbidity. In response to data received from the sensors 15 and analysis by the artificial intelligence processor 25, the decision processor 23 determines that the probability of Cyanobacteria in the water is 99.4%, the probability of Microcystin in the water is 93.9%, and the probability of other problem (for example water taste problem) is 22.7%.

In the fourth case, the sensor 15 detected Microcystin, a high level of chlorophyll, high temperature, high pH, high DO, and high turbidity. In response to data received from the sensors 15 and analysis by the artificial intelligence processor 25, the decision processor 23 determines that the probability of Cyanobacteria in the water is 100%, the probability of Microcystin in the water is 94.4%, and the probability of other problems (for example water taste problem) is 22.9%.

In the fifth case, the sensor 15 did not detect Microcystin, but detected a high level of chlorophyll, high temperature, high pH, high DO, and high turbidity. In response to data received from the sensors 15 and analysis by the artificial intelligence processor 25, the decision processor 23 determines that the probability of Cyanobacteria in the water is 100%, the probability of Microcystin in the water is 4.42%, and the probability of other problem (for example water taste problem) is 68.9%.

In the sixth case, the sensor 15 detected Microcystin, a normal level of chlorophyll, normal temperature, normal pH, normal DO, and normal turbidity. In response to data received from the sensors 15 and analysis by the artificial intelligence processor 25, the decision processor 23 determines that the probability of Cyanobacteria in the water is 0%, the probability of Microcystin in the water is 6.17%, and the probability of other problem (for example water taste problem) is 1.49%.

In the seventh case, the sensor 15 did not detect Microcystin, and detected a normal level of chlorophyll level, high temperature, high pH, normal DO, and high turbidity. In response to data received from the sensors 15 and analysis by the artificial intelligence processor 25, the decision processor 23 determines that the probability of Cyanobacteria in the water is 9.14%, probability of Microcystin in the water is 0.43%, probability of other problem (for example water taste problem) is 6.55%.

The decision processor 23 then interprets the different scenarios above and, based on the following rule set, generates an alarm and/or mitigation information to the appropriate users:

1. If the decision processor 23 reported between 2%-4% probability of Microcystin, then generate an alarm and report a high probability of Cyanobacteria in the water. Notify operators to be alert for possible Microcystin.

2. If the decision processor 23 reported between 4%-5% probability of Microcystin, then generate an alarm and report extremely high probability of Cyanobacteria in the water. Notify operators to be alert for possible Microcystin.

3. If the decision processor 23 reported 6.17% probability of Microcystin, then generate an alarm. Report that sensor 15 detected Microcystin but did not indicate Cyanobacteria in the water. Notify operators of possible sensor 15 error or terrorist attack.

4. If the decision processor 23 reported between 6.17%-10% probability of Microcystin, then generate an alarm and report that sensor 15 detected Microcystin and secondary factors for Cyanobacteria in the water.

5. If the decision processor 23 reported 10% or higher probability of Microcystin, then generate an alarm and report high probability of Microcystin in the water.

As another example, the following table outlines various sensor outputs that may indicate a possible chemical contamination. Benzene, Toluene, Metaxylene, Orthoxylene, Peraxylene, and MTBE are all components of gasoline. If a number of the above contaminants are detected it means a high probability that gasoline is present in the water. A high level of any of the listed contaminants will increase turbidity.

| | 1 | 2 | 3 | 4 | 5 | 6 | 7 | |
|---|---|---|---|---|---|---|---|---|
| Sensor_Benzene | True | True | True | True | True | True | True | True - toxin is detected<br>False - toxin is not detected |
| Sensor_Toluene | False | True | True | True | True | True | True | True - toxin is detected<br>False - toxin is not detected |
| Sensor_Metaxylene | False | False | True | True | True | True | True | True - toxin is detected<br>False - toxin is not detected |
| Sensor_Peraxylene | False | False | False | False | True | True | True | True - toxin is detected<br>False - toxin is not detected |
| Sensor_Orthoxylene | False | False | False | False | False | True | True | True - toxin is detected<br>False - toxin is not detected |
| Sensor_MTBE | False | False | False | False | False | True | True | True - toxin is detected<br>False - toxin is not detected |
| Turbidity | Normal | Normal | Normal | High | High | High | Normal | High - greater than 20 NTU<br>Normal - 0-20 NTU |
| Benzene | 91.0% | 91.0% | 91.3% | 98.3% | 100% | 100% | 100% | Above 30% - alert |
| Toluene | 0.001% | 91.0% | 91.3% | 98.3% | 100% | 100% | 100% | Above 30% - alert |
| Metaxylene | 0.001% | 0.001% | 91.3% | 98.3% | 100% | 100% | 100% | Above 30% - alert |
| Peraxylene | 0.001% | 0.001% | 0.34% | 7.9% | 100% | 100% | 100% | Above 30% - alert |
| Orthoxylene | 0.001% | 0.001% | 0.34% | 7.9% | 9.02% | 100% | 100% | Above 30% - alert |
| MTBE | 0.001% | 0.001% | 0.34% | 7.9% | 9.02% | 100% | 100% | Above 30% - alert |
| Gasoline | 0% | 0% | 3.74% | 80.9% | 100% | 100% | 100% | Above 2% - alert |

In the first case, the chemical sensors 15 detect benzene in the water and a normal turbidity level. In response to data received from the sensors 15 and analysis by the artificial intelligence processor 25, the decision processor 23 determines that the probability of benzene in the water is 91.0%, the probability of toluene in the water is 0.001%, the probability of metaxylene in the water is 0.001%, the probability of peraxylene in the water is 0.001%, the probability of orthoxylene in the water is 0.001%, the probability of MTBE in the water is 0.001%, and the probability of gasoline in the water is 0%.

In the second case, the chemical sensors 15 detect benzene and toluene in the water, with a normal turbidity level. In response to data received from the sensors 15 and analysis by the artificial intelligence processor 25, the decision processor 23 determines that the probability of benzene in the water is 91.0%, the probability of toluene in the water is 91.0%, the probability of metaxylene in the water is 0.001%, the probability of peraxylene in the water is 0.001%, the probability of orthoxylene in the water is 0.001%, the probability of MTBE in the water is 0.001%, and the probability of gasoline in the water is 0%.

In the third case, the chemical sensors 15 detect benzene, toluene and metaxylene in the water, with a normal turbidity level. In response to data received from the sensors 15 and analysis by the artificial intelligence processor 25, the decision processor 23 determines that the probability of benzene in the water is 91.3%, the probability of toluene in the water is 91.3%, the probability of metaxylene in the water is 91.3%, the probability of peraxylene in the water is 0.34%, the probability of orthoxylene in the water is 0.34%, the probability of MTBE in the water is 0.34%, and the probability of gasoline in the water is 3.74%.

In the fourth case, the chemical sensors 15 detect benzene, toluene, and metaxylene in the water, with a high turbidity level. In response to data received from the sensors 15 and analysis by the artificial intelligence processor 25, the decision processor 23 determines that the probability of benzene in the water is 98.3%, the probability of toluene in the water is 98.3%, the probability of metaxylene in the water is 98.3%, the probability of peraxylene in the water is 7.9%, the probability of orthoxylene in the water is 7.9%, the probability of MTBE in the water is 7.9%, and the probability of gasoline in the water is 80.9%.

In the fifth case, the chemical sensors 15 detect benzene, toluene, metaxylene and peraxylene in the water, with a high turbidity level. In response to data received from the sensors 15 and analysis by the artificial intelligence processor 25, the decision processor 23 determines that the probability of benzene in the water is 100%, the probability of toluene in the water is 100%, the probability of metaxylene in the water is 100%, the probability of peraxylene in the water is 100%, the probability of orthoxylene in the water is 9.02%, the probability of MTBE in the water is 9.02%, and the probability of gasoline in the water is 100%.

In the sixth case, the chemical sensors 15 detect benzene, toluene, metaxylene, peraxylene, orthoxylene and MTBE in the water, with a high turbidity level. In response to data received from the sensors 15 and analysis by the artificial intelligence processor 25, the decision processor 23 determines that the probability of benzene in the water is 100%, the probability of toluene in the water is 100%, the probability of metaxylene in the water is 100%, the probability of peraxylene in the water is 100%, the probability of orthoxylene in the water is 100%, the probability of MTBE in the water is 100%, and the probability of gasoline in the water is 100%.

In the seventh case, the chemical sensors 15 detect benzene, toluene, metaxylene, peraxylene, orthoxylene and MTBE in the water, with a normal turbidity level. In response to data received from the sensors 15 and analysis by the artificial intelligence processor 25, the decision processor 23 determines that the probability of benzene in the water is 100%, the probability of toluene in the water is 100%, the probability of metaxylene in the water is 100%, the probability of peraxylene in the water is 100%, the probability of orthoxylene in the water is 100%, the probability of MTBE in the water is 100%, and the probability of gasoline in the water is 100%.

The decision processor 23 then interprets the different scenarios above and, based on the following rule set, generates an alarm and/or mitigation plan to the user interface module 13 as follows:

1. If two or fewer contaminants are detected, then generate an alarm and report that particular contaminants are detected.

2. If more than two contaminants are detected, then generate an alarm and report that particular contaminants are detected and that there is possible gasoline in the water.

3. If more than two contaminants are detected and turbidity level is high, then generate an alarm and report that particular contaminants are detected and there is a high probability of gasoline in the water.

4. If more than three contaminants are detected, then generate an alarm and report that particular contaminants are detected and that there is a high level of gasoline in the water.

For each particular contaminant or group of contaminants (which have relatively similar data-patterns from readings) three types of rules must be used: (1) rules to show the relationship between data from sensors 15 and particular contaminant, (2) rules to evaluate the report from the artificial intelligence processor 25 analysis of the sensor 15 signals, interpret it and classify it as different types of problem, and (3) rules for suggesting a particular mitigation plan.

What is claimed is:

1. An apparatus for detecting and warning of a chemical or biological contaminant in a body of water, comprising:
   a monitoring module comprising a plurality of sensors positioned in said body of water, wherein each said sensor is adapted to sense a respective environmental parameter and to output data regarding said parameter, and a data transmitting unit coupled to said plurality of sensors for transmitting said data; and
   a decision support module adapted to receive said data from said data transmitting unit, said decision support module comprising a relational database for storing said data and at least one rule for processing said data, an artificial intelligence processor programmed to identify trends in said data over time, and a decision processor interconnected to said relational database and said artificial intelligence processor that is programmed to apply the at least one rule for processing said data to determine the probability of the presence of said contaminant.

2. The apparatus of claim 1, further comprising a first communications network for transmitting said data from said plurality of sensors to said processor.

3. The apparatus of claim 2, wherein said processor generates a signal when said probability exceeds a predetermined threshold.

4. The apparatus of claim 3, wherein said threshold is a user-defined threshold.

5. The apparatus of claim 3, wherein said signal is variable in relation to the magnitude of said probability.

6. The apparatus of claim 3, further comprising a second communications network for transmitting said signal to a remote location.

7. The apparatus of claim 3, wherein said signal communicates information to identify the specific contaminant.

8. The apparatus of claim 3, wherein said signal communicates information for mitigating the specific contaminant.

9. The apparatus of claim 1, wherein the specific condition contaminant is a first contaminant that has a high probability of producing a second contaminant after a period of time.

10. The apparatus of claim 1, wherein said artificial intelligence system comprises an inference engine.

11. The apparatus of claim 1 further comprising a display having color coded indicators for providing information about the presence of said condition, in response to said signal.

12. An apparatus for detecting and warning of the presence of hazardous biological or chemical contaminants in water, comprising:
   a plurality of sensors for detecting a plurality of environmental parameters, each sensor generating a first signal in response to said environmental parameters;
   a processor for receiving each said first signal, said processor comprising an artificial intelligence module programmed to identify trends in said data over time and a decision module programmed to apply at least one rule for processing said data to determine the probability of the presence of said contaminant;
   a relational database for storing said data and the said least one rule for processing said data; and
   wherein said processor generates a second signal when said probability exceeds a predetermined threshold.

13. The apparatus of claim 12, wherein said threshold is a user-defined threshold.

14. The apparatus of claim 12, wherein said second signal is variable in relation to the magnitude of said probability.

15. The apparatus of claim 12, further comprising a first communications network for transmitting said plurality of first signals to said processor.

16. The apparatus of claim 12, further comprising a second communications network for transmitting said second signal to a remote location.

17. The apparatus of claim 12, wherein said second signal identifies said contaminant.

18. The apparatus of claim 12, wherein said artificial intelligence system comprises an inference engine.

19. The apparatus of claim 12 further comprising a display having color coded indicators for providing information about the presence of said hazardous condition, in response to said second signal.

20. An apparatus for predicting the occurrence of a specific biological or chemical contaminant in a body of water, comprising:
   a plurality of sensors for detecting a plurality of environmental parameters, each sensor generating a first signal in response to one of said environmental parameters;
   a processor for receiving each said first signal, said processor comprising an artificial intelligence sensors module programmed to identify trends in said data over time and a decision module programmed to apply at least one rule for processing said data to determine the probability that the presence of said contaminant will occur;
   a relational database for storing said data and the said least one rule for processing said data; and
   wherein said processor generates a second signal when said probability exceeds a predetermined threshold.

21. The apparatus of claim 20, wherein said threshold is a user-defined threshold.

22. The apparatus of claim 20, wherein said second signal is variable in relation to the magnitude of said probability.

23. The apparatus of claim 20, further comprising a first communications network for transmitting said plurality of first signals to said processor.

24. The apparatus of claim 20, further comprising a second communications network for transmitting said second signal to a remote location.

25. The apparatus of claim 20, wherein said second signal identifies said specific condition.

26. The apparatus of claim 20, wherein said artificial intelligence system comprises an inference engine.

27. The apparatus of claim 20 further comprising a display having color coded indicators for providing information about the likelihood of said condition, in response to said second signal.

* * * * *